(12) United States Patent
Roe

(10) Patent No.: US 6,414,215 B1
(45) Date of Patent: *Jul. 2, 2002

(54) DISPOSABLE ABSORBENT ARTICLE HAVING CAPACITY TO STORE LOW-VISCOSITY FECAL MATERIAL

(75) Inventor: Donald C. Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/437,037

(22) Filed: Nov. 9, 1999

Related U.S. Application Data

(63) Continuation of application No. 08/108,944, filed on Aug. 17, 1993, now abandoned.

(51) Int. Cl.[7] .................................................. A61F 13/15
(52) U.S. Cl. .................. 604/378; 604/384; 604/385.01; 604/385.101; 604/385.23
(58) Field of Search ............................ 604/378, 385.01, 604/384, 385.101, 385.23

(56) References Cited

U.S. PATENT DOCUMENTS

| 4,704,112 A | | 11/1987 | Suzuki et al. | |
|---|---|---|---|---|
| 5,941,864 A | * | 8/1999 | Roe | 604/378 |
| 6,190,369 B1 | * | 2/2001 | Palumbo et al. | 604/385.01 |

\* cited by examiner

Primary Examiner—John G. Weiss
Assistant Examiner—Jacqueline Stephens
(74) Attorney, Agent, or Firm—Michael P. Hayden; David M. Weirich; Ken K. Patel

(57) ABSTRACT

A disposable absorbent article, such as a diaper. The disposable absorbent article has a first topsheet with apertures large enough for low-viscosity fecal material to pass through to a fecal material storage element. The fecal material storage element immobilizes the fecal material in position for dewatering, so that the liquid components of the fecal material are absorbed by the core and the solid components of the fecal material are separated from the liquid components. This arrangement provides for easier cleaning of the wearer when the soiled disposable absorbent article is removed.

20 Claims, 3 Drawing Sheets

DISPOSABLE ABSORBENT ARTICLE HAVING CAPACITY TO STORE LOW-VISCOSITY FECAL MATERIAL

This application is a continuation of U.S. Application Ser. No. 08/108,944 filed on Aug. 17, 1993 in the name of Donald C. Roe, and abandoned on Jan. 5, 2000.

FIELD OF THE INVENTION

This invention relates to disposable absorbent articles, such as diapers and adult incontinence products, and more particularly to disposable absorbent articles which have the capacity to retain low-viscosity fecal material away from the skin of the wearer, in order to reduce leakage and make it easier to clean the wearer when the soiled disposable absorbent article is removed.

BACKGROUND OF THE INVENTION

Disposable absorbent articles such as diapers and adult incontinence products are well known in the art. Such disposable absorbent articles collect and retain urine and fecal material deposited thereon by the wearer.

To date, most attempts in the art to handle the urine and fecal material collected and retained in the disposable absorbent article have been directed to handling urine. Dealing with fecal material collected by the disposable absorbent article is simply more difficult than dealing with urine, due to the complex rheology of low-viscosity fecal material.

Exemplary of the urine handling prior art are several attempts to provide disposable absorbent articles having a first topsheet which faces towards and contacts the body of the wearer, and a secondary topsheet under the first topsheet, which either absorbs urine, or transfers the urine to an underlying core for storage until the disposable absorbent article is removed from the wearer.

Typically, the first topsheet and secondary topsheet have different material properties. The secondary topsheet may have a smaller pore size than the first topsheet, to assist in transfer of the urine through the topsheet. The first topsheet may be hydrophobic and more resilient when wetted than the secondary topsheet, in order to pass fluids through the first topsheet to the secondary topsheet.

In yet another attempt in the prior art, the disposable absorbent article has a first topsheet, secondary topsheet and core. The secondary topsheet consists essentially of melt-blown hydrophilic fibers and has a pore size greater than the pore size of the core. This arrangement allegedly allows the secondary topsheet to rapidly receive multiple liquid insults and distribute the liquid in the X-Y plane prior to absorption by the core. In yet another attempt, improved vertical wicking capability for urine has been allegedly achieved using inflated cellulose fibers which are free of a surface finish or are crosslinked to one another.

In another attempt in the prior art, an absorbent core suitable for acquiring and containing liquids such as urine in a particularly effective and efficient manner comprises multiple layers. The first layer, which is closest to the wearer, comprises hydrophilic fibrous material and has an acquisition zone of a relatively lower average density than other portions of this layer, in order to quickly acquire discharged liquids. Below the first layer is a liquid handling layer comprising a resilient, low density high void volume material that is moisture insensitive in order to rapidly acquire liquid insults into itself through the acquisition zone and distribute these liquids throughout the liquid handling layer to a storage layer. The storage layer comprises a combination of fibrous material and discrete particles of absorbent gelling material, and allows the liquid handling layer to be drained of the liquids it has acquired, so that the liquid handling layer may have sufficient capacity to acquire and distribute subsequent loadings of liquids.

Examples of such attempts in the prior art include U.S. Pat. No. 4,047,531 issued Sep. 13, 1977 to Karami; U.S. Pat. No. 4,798,603 issued Jan. 17, 1989 to Meyer et al.; U.S. Pat No. 5,037,409 issued Aug. 6, 1991 to Chen et al.; U.S. Pat. No. 5,124,197 issued Jun. 23, 1992 to Bernardin et al.; and U.S. Pat No. 5,134,007 issued Jul. 28, 1992 to Reising et al.

Of course, absorbent gelling materials are also now well known in the prior art for their urine handling capability. Absorbent gelling materials are polymeric materials capable of absorbing large quantities of fluids, such as urine, and retaining such absorbed fluids under moderate pressure. The effectiveness of the absorbent gelling materials is quite dependent upon the form, position, and weight percentage of the absorbent gelling materials which are incorporated into the core of the disposable absorbent article.

Recent attempts have been made in the art to provide absorbent gelling materials which have the ability to swell against pressure. These teachings allege to provide the advantage that the absorbent gelling materials absorb fluid under actual pressures exerted by the body during use. Yet other teachings in the art provide absorbent gelling materials having a particular free swell rate and absorbency under load. Alleged advantages of such an absorbent gelling materials are lower volume and mass with approximately the same absorbent capacity, the ability to rapidly absorb a discharged liquid under pressures typically encountered during use, and the ability to retain the absorbed liquid under pressures typically encountered during use.

Examples of such attempts in the prior art include U.S. Pat. No. 5,147,343 issued Sep. 15, 1992 to Kellenberger and U.S. Pat. No. 5,149,335 issued Sep. 22, 1992 to Kellenberger et al.

However, all of these attempts to handle urine do little, if anything, to improve handling of low-viscosity fecal material which may also be present in the disposable absorbent article. Attempts to deal with fecal material include providing a first topsheet which conforms closely to the wearer and has an aperture. The aperture is hopefully registered with the anal opening, so that fecal material passes therethrough into a void space. The first topsheet may comprise various elastic panels in order to closely conform to the skin of the wearer, and/or may have linear elastic strands. Improvements have been made in this area of the prior art, such as optimizing the material properties of the first topsheet. Such optimization makes the first topsheet more comfortable to the wearer and allows a single disposable absorbent article to fit a larger range of sizes of wearers.

Yet other attempts have been made in this area of the prior art to provide an absorbent core with a hole therein, in order to receive the fecal material. The hole may be oblate shaped, so that it is longer and narrower than the aperture in the first topsheet, or may be diamond shaped. The hole in the core may be positioned below an aperture which has elastic strips around its edge.

Improvements to this genre of the prior art disposable absorbent articles also include the addition of spacers. Spacers may be interposed between the first topsheet and the core, in order to ensure a void space is present to receive the fecal material.

Yet other attempts have been made in this genre of the prior art to provide barriers which limit the movement of fecal material to particular portions of the disposable absorbent article. The barriers limit the contact of the fecal material to a lesser portion of the skin of the wearer, than a comparable disposable absorbent article which has no barriers.

Still other attempts in the prior art provide barrier leg cuffs which are upstanding from the plane of the topsheet. The barrier leg cuffs prevent fecal material from breaching the perimeter of the disposable absorbent article.

Examples of such attempts to handle fecal material include U.S. Pat. No. 4,892,536 issued Jan. 9, 1990 to DesMarais et al.; U.S. Pat. No. 4,909,803 issued Mar. 20, 1990 to Aziz et al.; U.S. Pat. No. 4,968,312 issued Nov. 6, 1990 to Khan; commonly assigned U.S. Pat. No. 4,990,147 issued Feb. 5, 1991 to Freeland; commonly assigned U.S. Pat. No. 5,037,416 issued Aug. 6, 1991 to Allen et al.; U.S. Pat. No. 5,062,840 issued Nov. 5, 1991 to Holt et al.; commonly assigned U.S. Pat. No. 5,171,236 issued Dec. 15, 1992 to Dreier et al.; and European Patent Application 0,355,740 A2 published Feb. 28, 1990 to Enloe.

However, none of these attempts to handle fecal material solve the problem of low-viscosity fecal material which is prevalent in younger children, particularly those who are breast fed. Low-viscosity fecal material easily migrates within the disposable absorbent article under the influences of gravity and motion or pressure by the wearer.

The migration of the fecal material often moves it towards the perimeter of the disposable absorbent article, increasing the likelihood of leakage. The migration of the fecal material also smears it against the skin of the wearer, making cleanup more difficult. In order to clean the wearer, the caretaker must wipe the entire area of the skin which has encountered the fecal material and typically has to deal with a relatively large soiled area.

One serious attempt in the art to handle low-viscosity fecal material is found in U.S. Pat. application Ser. No. 08/076,713 filed Jun. 11, 1993 in the name of Roe, which matured into U.S. Pat. No. 5,342,338 issued to Roe on Aug. 30, 1994. This application is for a disposable absorbent article having a first topsheet with a high trans-topsheet penetration overlying a secondary topsheet having a lesser trans-topsheet penetration.

Accordingly, it is an object of this invention to provide a disposable absorbent article which reduces leakage of fecal material from the disposable absorbent article and minimizes the amount of low-viscosity fecal material remaining on the skin of the wearer once the disposable absorbent article is removed. It is further an object of this invention to provide a disposable absorbent article which separates the fecal material into components.

BRIEF SUMMARY OF THE INVENTION

The invention is a disposable absorbent article, such as a diaper. The disposable absorbent article comprises a liquid pervious first topsheet, a liquid impervious backsheet at least partially peripherally joined to the first topsheet, and a fecal material storage element intermediate the first topsheet and the backsheet. The fecal material storage element may be absorbent or nonabsorbent and may either be incorporated into or separate from an absorbent core. The fecal material storage element is preferably bonded to less than 50 percent of the surface area of the first topsheet.

The disposable absorbent article has a trans-topsheet capacity of at least 0.20 grams per square inch at a differential pressure of 0.071 pounds per square inch over a surface area of at least about 30 square inches, and preferably over an area at least about 45 square inches. The minimum and preferred surface areas decrease in inverse relationship to the trans-topsheet capacity as it increases.

If the disposable absorbent article further comprises an absorbent core, it may be intermediate the first topsheet and the backsheet, and preferably intermediate the fecal material storage element and backsheet.

BRIEF DESCRIPTION OF THE DRAWINGS

While the Specification concludes with claims pointing out and distinctly claiming the present invention, it is believed the same will be better understood by the following drawings taken in conjunction with the accompanying Specification wherein like components are given the same reference number and:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and adult incontinent persons and is worn about the lower torso of the wearer.

Figure 1:
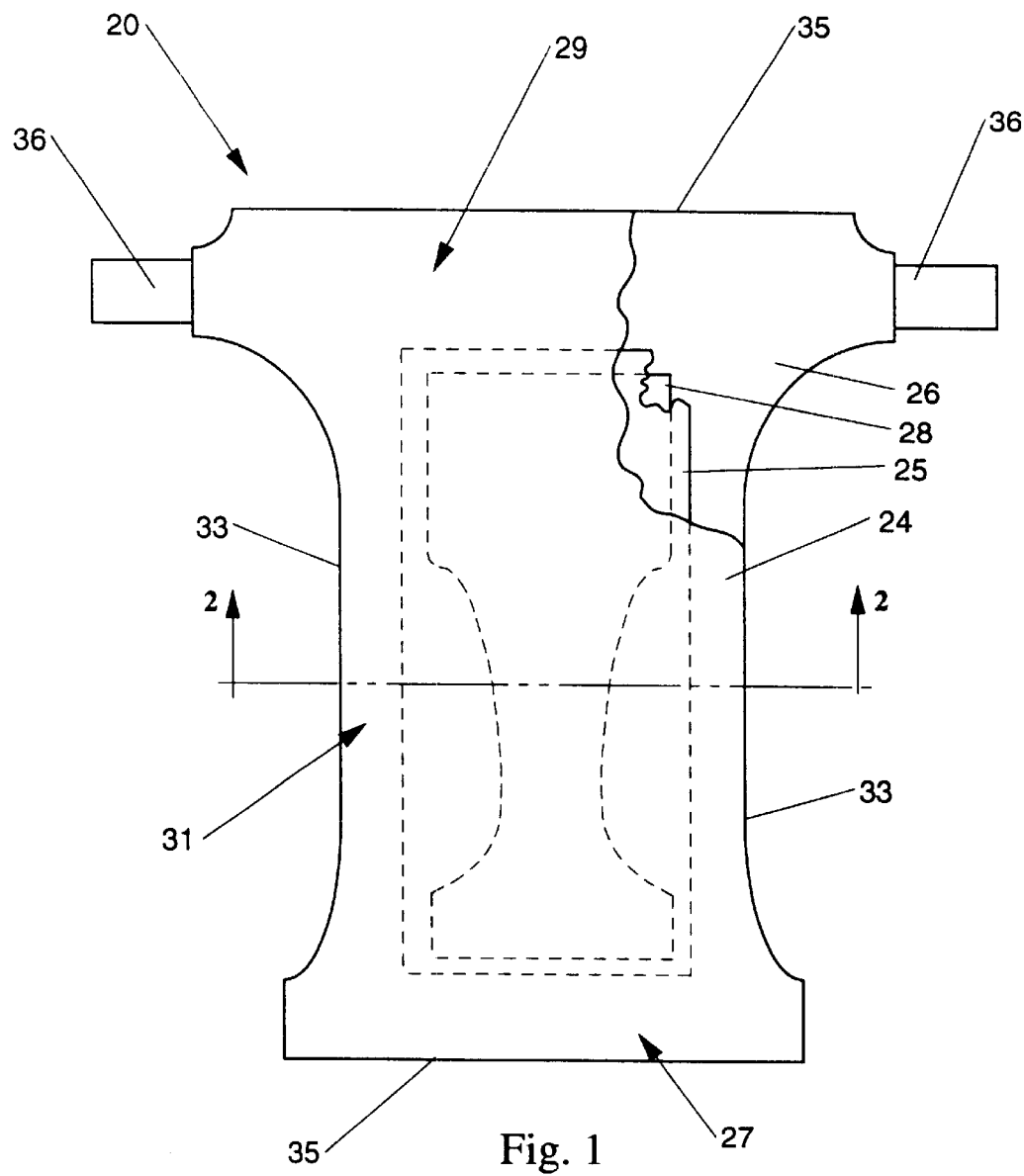
FIG. 1 is a top plan view, shown partially in cutaway, of a disposable absorbent article according to the present invention.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 1, the diaper 20 preferably comprises a liquid pervious first topsheet 24; a liquid impervious backsheet 26 joined with the first topsheet 24; a liquid pervious fecal material storage element 25 intermediate the first topsheet 24 and the backsheet 26; and optionally an absorbent core 28 intermediate the fecal material storage element 25 and the backsheet 26. Either the core 28, a separate component, or a combination thereof, may function as the fecal material storage element 25, so that the diaper 20 has the trans-topsheet capacity described below. The diaper 20 may further comprise elasticized side panels (not shown); elasticized leg cuffs (not shown); an elastic waist feature (not shown); and a fastening system with tape tabs generally multiply designated as 36.

The diaper 20 is shown in FIG. 1 to have a first waist region 27 juxtaposed with the front of the wearer while the diaper 20 is being worn, a second waist region 29 opposed to the first waist region 27 and juxtaposed with the back of the wearer while the diaper 20 is being worn, a crotch region 31 positioned between the first waist region 27 and the second waist region 29, and a periphery which is defined by the outer edges of the diaper 20 in which the longitudinal edges are designated 33 and the end edges are designated 35. The inner surface of the diaper 20 comprises that portion of the diaper 20 which is adjacent to the wearer's body during use (i.e., the inner surface generally is formed by at least a portion of the first topsheet 24 and other components joined to the first topsheet 24). The outer surface comprises that portion of the diaper 20 which is positioned away from the wearer's body (i.e., the outer surface generally is formed by at least a portion of the backsheet 26 and other components joined to the backsheet 26) during use.

Figure 2:
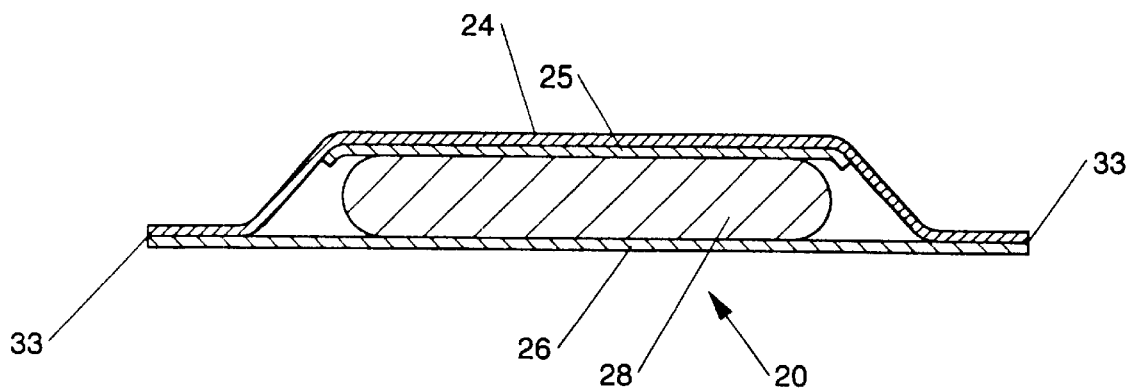
FIG. 2 is a vertical sectional view taken along line 2—2 of FIG. 1, showing the relationship of the first topsheet, fecal material storage element and core.

FIG. 2 shows an embodiment of the diaper 20 in which the first topsheet 24 and the backsheet 26 have length and width dimensions generally larger than those of the absorbent core 28. The first topsheet 24 and the backsheet 26 extend beyond the edges of the absorbent core 28 to thereby form the periphery of the diaper 20. Alternatively, the fecal material storage element 25 may, but need not, extend beyond the edges of the core 28 and be joined to the backsheet 26 to form the periphery of the diaper 20 and the first topsheet 24 smaller than or coextensive of the core 28. While the first topsheet 24, the fecal material storage element 25, the backsheet 26, and the core 28 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. Pat. No. 5,151,092, "Absorbent Article With Dynamic Elastic Waist Feature Having A Predisposed Resilient Flexural Hinge", issued to Kenneth B. Buell et al. Sep. 29, 1992; each of which is incorporated herein by reference.

The absorbent core 28 may be any absorbent means which is generally compressible, conformable, non-irritating to the wearer's skin, and capable of absorbing and retaining liquids such as urine and other certain body exudates. As shown in FIG. 1, the absorbent core 28 has a garment surface, a body surface, side edges, and waist edges. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may also be varied (e.g., the absorbent core 28 may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults.

Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents is incorporated herein by reference.

The backsheet 26 is positioned adjacent the garment surface of the absorbent core 28 and is preferably joined thereto by attachment means (not shown) such as those well known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to is Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body.

The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet 26 is a thermoplastic film having a thickness of about 0.012 mm (0.5 mil) to about 0.051 mm (2.0 mils).

Particularly preferred materials for the backsheet 26 include RR8220 blown films and RR5475 cast films as manufactured by Tredegar Industries, Inc. of Terre Haute, Ind. The backsheet 26 is preferably embossed and/or matte finished to provide a more clothlike appearance. Further, the backsheet 26 may permit vapors to escape from the absorbent core 28 (i.e., be breathable) while still preventing exudates from passing through the backsheet 26.

The first topsheet 24 and the fecal material storage element 25 each have two major faces. The first topsheet 24 has a first major face oriented towards the wearer and an opposed second major face oriented towards the fecal material storage element 25. The fecal material storage element 25 has a first major face oriented towards the first topsheet 24, and an opposed second major face oriented towards the core 28, if it is separate from the fecal material storage element 25.

The first topsheet 24 is juxtaposed with, but not necessarily adjacent the body surface of the fecal material storage element 25, and is preferably joined to the backsheet 26 or fecal material storage element 25 by means such as those well known in the art. Suitable attachment means are described above with respect to joining the backsheet 26 to the absorbent core 28. In a preferred embodiment of the present invention, the first topsheet 24 and the backsheet 26 are joined directly to each other in the diaper periphery.

The first topsheet 24 is compliant, soft feeling, and nonirritating to the wearer's skin. Further, the first topsheet 24 is liquid pervious, permitting liquids (e.g., urine) to readily penetrate through its thickness. A suitable first topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the first topsheet 24 is made of a hydrophobic material to isolate the wearer's skin from liquids contained in the absorbent core 28. Alternatively, the topsheet 24 may be surfactant treated to make it hydrophilic.

There are a number of manufacturing techniques which may be used to manufacture the first topsheet 24. For example, the first topsheet 24 may be a nonwoven web of fibers spunbonded, carded, wet-laid, meltblown, hydroentangled, combinations or composite laminates of the above, or the like. Preferred first topsheets 24 include a carded/carded composite, hydroentangled over a wire forming screen and thermally air-through bonded by means well known to those skilled in the nonwovens art and hydroentanglement of fibrous webs. Alternatively, apertured formed films may be suitable.

The diaper 20 has a minimum trans-topsheet capacity dependent upon the surface area of the first topsheet 24 having this minimum trans-topsheet capacity. Of course, the trans-topsheet capacity need not be the same throughout all areas of the diaper 20. For example, the regions of the diaper 20 registered with the anal opening may have a relatively higher trans-topsheet capacity than the outlying regions of the diaper 20.

There is an inverse relationship between the minimum trans-topsheet capacity necessary to handle low-viscosity fecal material and the surface area of the diaper 20 having this minimum capacity. As a larger percentage of the diaper 20 surface area has a trans-topsheet capacity sufficient to handle low-viscosity fecal material, the necessary trans-topsheet capacity diminishes.

In any case, the diaper 20 should have a trans-topsheet capacity of at least about 0.20 grams per square inch providing at least 30 square inches of the diaper 20 has such a trans-topsheet capacity and preferably at least 45 square inches of the diaper 20 has such a trans-topsheet capacity. It is believed that a minimum of 4 square inches of the diaper 20, which are closely registered with the anal opening, are necessary to handle low-viscosity fecal material. If such a relatively small region of the diaper 20 is provided, this region of the diaper 20 should have a trans-topsheet capacity of at least about 0.50 and preferably at least about 0.60 grams per square inch.

The trade-off between trans-topsheet capacity and minimum surface area for a diaper 20 according to the present invention which is necessary to handle low-viscosity fecal material and the preferred surface area for a diaper 20 according to the present invention is illustrated in Table I below:

TABLE I

| Trans-topsheet Capacity (grams/square inch) | Minimum Diaper Surface Area Having This Trans-topsheet Capacity (square inches) | Preferred Diaper Surface Area Having This Trans-topsheet Capacity (square inches) |
| --- | --- | --- |
| 0.20 | 30 | 45 |
| 0.30 | 15 | 25 |
| 0.40 | 12 | 20 |
| 0.50 | 4 | 10 |
| 0.60 | 4 | 4 |

Figure 3:
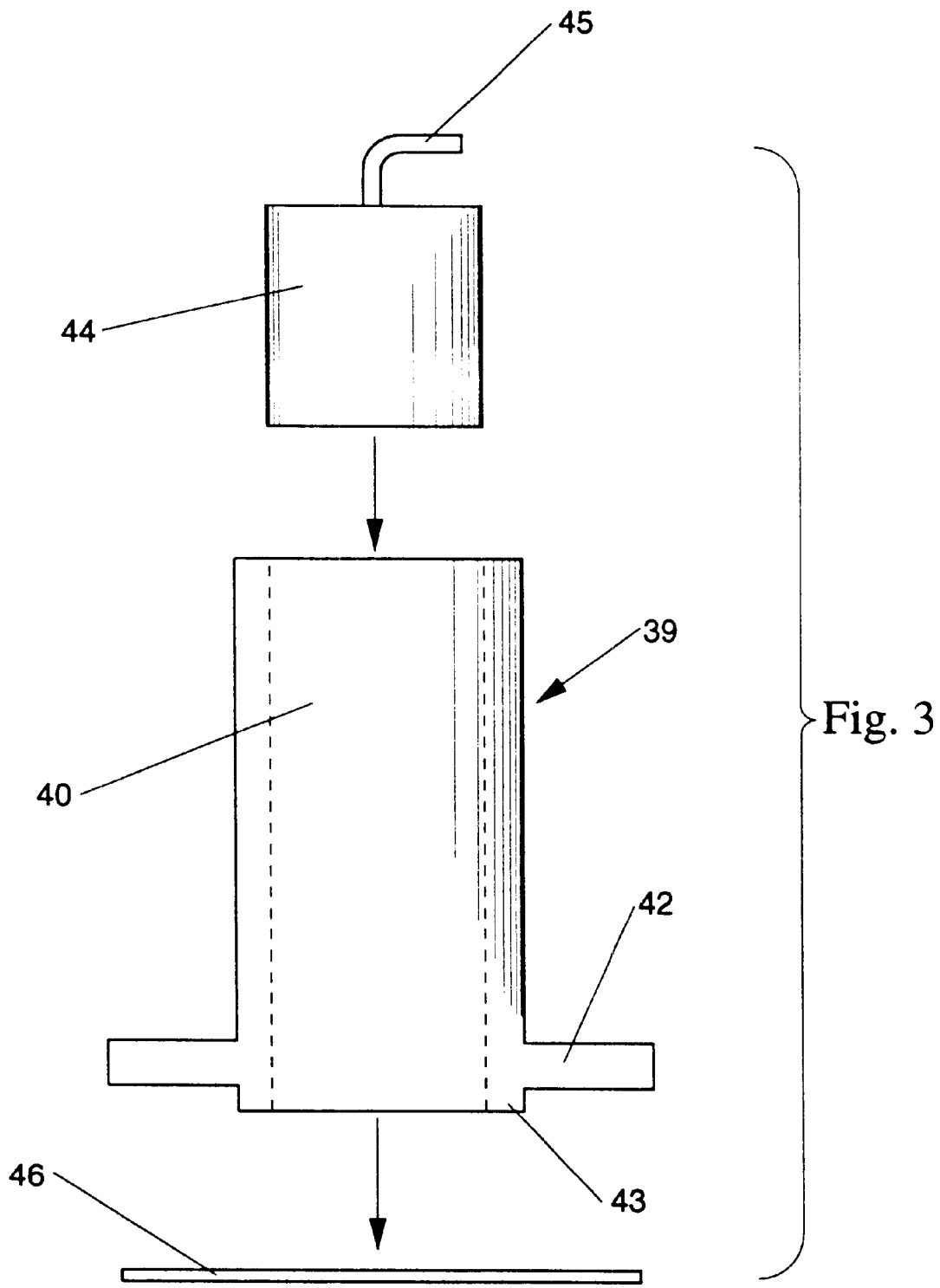
FIG. 3 is a schematic side elevational view of an apparatus which may be used to measure the capacity of the disposable absorbent article.

Trans-topsheet capacity is measured by the following test. The apparatus 39 used for this measurement is illustrated in FIG. 3.

A hollow stainless steel cylinder 40 mounted on a plate 42 is provided. The stainless steel cylinder 40 has a height of 7.5 centimeters (2.95 inches), an inside diameter of 5.08 centimeters (2.00 inches) and an outside diameter of 6.3 centimeters (2.48 inches). The bottom of the cylinder 40 extends below the plate a distance of 3.5 millimeters, and has a lip with an annular thickness of 3.5 millimeters. The lip 43 prevents the fecal material analog, discussed below, from leaking outside the designated test area of the sample.

Also provided is a weight 44 of 100.6 grams. The weight 44 is also cylindrically shaped and has a diameter of 5.08 centimeters (2.0 inches), so that the weight 44 fits tightly within the cylinder 40 but can freely slide throughout the hole in the cylinder 40. This arrangement provides a pressure of 49.57 kilograms per square meter (0.071 pounds per square inch) and a test area of 3.142 square inches. If desired, the weight 44 may have a handle 45 to allow it to be easily inserted into and removed from the cylinder 40.

A sample 46 to be tested is provided. The sample 46 is preferably cut from an existing diaper 20, but prophetically may be supplied in raw material form as a laminate of the various components of the diaper 20. The sample 46 is cut to a 10.16 by 10.16 centimeters (4 by 4 inch) square size. The sample 46 is taken from any area of the diaper 20 having the absorbent core 28 inside the square which defines the sample 46.

If the sample 46 is cut from a diaper 20, the sample should include all layers and components of the diaper 20 from the first topsheet 24 through and including the backsheet 26. Care must be taken when removing the sample 46 from the diaper 20 not to destroy the sample 46 or cause unintended gross deformation of the first topsheet 24. The first topsheet 24, or its equivalent in the diaper 20, is removed from the balance of the sample 46. The sample 46 (without the first topsheet 24) is weighed to the nearest 0.01 grams. The first topsheet 24 is then carefully returned to its original position in the sample 46, without being joined thereto. If difficulty is encountered in removing the sample 46 from the diaper 20, or in removing the first topsheet 24 from the sample 46, the sample 46 and the surrounding portion of the diaper 20 may be frozen prior to or after cutting. Freezing may be accomplished using PH100-15 circuit refrigerant made by Philips ECG, Inc. of Waltham, Mass.

The cylinder 40 is centered on the sample 46. A syringe having an opening of 5 to 6 millimeters dispenses 10 cubic centimeters of test fluid through the hole in the cylinder 40 onto the top of the sample 46. The test fluid is an analog formulated as described below. The 100.6 gram weight 44 is inserted through the hole in the cylinder 40 and gently placed on the test fluid for a period of 2 minutes.

After 2 minutes the weight 44 and cylinder 40 are removed from the sample 46. The first topsheet 24 is removed from the sample 46 by dragging the first topsheet 24 parallel to the sample 46 and discarded. The remainder of the sample 46 is then reweighed. The trans-topsheet capacity is the increase in weight of all layers of the sample 46 underlying the first topsheet 24 divided by the sample 46 test area of 3.142 square inches.

The test fluid is an analog made by mixing 3 percent by weight Carbopol 941 available from the B. F. Goodrich Corporation of Brecksville, Ohio, or an equivalent acrylic polymer, in distilled water for five minutes using a hand held electric mixer. The mixture is allowed to equilibrate for at least 12 hours and used for the trans-topsheet capacity test within 72 hours.

To verify the methods of the claimed invention, four diapers 20 according to the prior art and six diapers 20 according to the present invention were tested. The diapers 20 according to the prior art achieved a trans-topsheet capacity of 0.09 grams per square inch or less. On the other hand, the diapers 20 according to the present invention achieved a trans-topsheet capacity of 0.20 grams per square inch. The diapers 20 according to the present invention utilized various topsheets and fecal material storage elements 25, with a piece of Eaton-Dikeman number 989 filter paper from Eaton-Dikeman, Division of Knowlton Brothers of Mount Holly Springs, Pa. disposed underneath to represent a separate absorbent core 28. It was felt that the filter paper would impede the flow of the analog used for the test fluid, making the test more rigorous for the diapers 20 according to the present invention.

The results are illustrated in Table II below. The first column of Table II gives the type of diaper 20 according to the prior art or, alternatively, the type of first topsheet 24/fecal material storage element 25 of the diaper 20 according to the present invention. The second column of Table II gives the trans-topsheet capacity in terms of grams per square inch. The first four entries in Table II represent diapers 20 currently available according to the prior art. The last six entries represent prototype diapers 20 according to the present invention. The first topsheet 24 construction is separated from the fecal material storage element 25 construction by a "/" in the last six entries. The filter paper represents the core 28 in the diapers 20 according to the present invention. The fecal material storage elements 25 in entries 5–6 are absorbent. The fecal material storage elements 25 in entries 7–10 are nonabsorbent. The foam absorbent material listed in the sixth entry was made according to Example 2A of commonly assigned U.S. patent application Ser. No. 08/082,861, filed Jun. 25, 1993 in the names of LaVon et al, the disclosure of which is incorporated herein by reference. It is noted that this Application matured into U.S. Pat. No. 5,397,316 issued to Lavon et al. on March 14, 1995.

TABLE II

| | Diaper | Trans-topsheet Capacity (grams per square inch) |
|---|---|---|
| 1 | Pampers Phases Available from The Procter & Gamble Company, Cincinnati, Ohio | 0.05 |
| 2 | Huggies Super Trim Available from Kimberly-Clark, Dallas, Texas | 0.06 |
| 3 | Huggies Baby Steps Available from Kimberly-Clark, Dallas, Texas | 0.07 |
| 4 | Huggies Ultra Trim Available from Kimberly-Clark, Dallas, Texas | 0.09 |
| 5 | Topsheet from Always Sanitary Napkin from The Procter & Gamble Company,/ 60 pounds per 3,000 square foot basis weight cellulosic fecal material storage element having blind apertures with a major dimension of 4 millimeters, a minor dimension of 2 millimeters and a depth of 0.75 millimeters | 0.21 |
| 6 | Topsheet from Always Sanitary Napkin from The Procter & Gamble Company,/ core was slit foam absorbent material as described herein by reference. | 0.38 |
| 7 | ACC 7192.36.1 from Fiberweb N.A., Simpsonville, South Carolina/ X5790 film from Tredegar Corporation of Terre Haute, Indiana | 0.47 |
| 8 | Topsheet from Always Sanitary Napkin/X5790 film from Tredegar Corporation of Terre Haute, Indiana | 0.63 |
| 9 | AMC 7191.26.1 from Fiberweb N.A., Simpsonville, South Carolina/X5790 film from Tredegar Corporation of Terre Haute, Indiana | 0.69 |
| 10 | Pantex 18125X from Fater Corporation of Pescara, Italy/X5790 film from Tredegar Corporation of Terre Haute, Indiana | 0.79 |

The diaper 20 according to the present invention preferably provides a trans-topsheet capacity, as measured by the foregoing test, of at least 0.20 grams per square more preferably at least 0.30 grams per square inch, even more preferably at least grams per square inch, still more preferably at least 0.50 grams per square inch, and preferably at least 0.60 grams per square inch.

The first topsheet 24 may allow penetration of the fecal material to achieve the trans-topsheet capacities set forth in Table I, by having apertures 58 with an effective aperture 58 size of at least 0.2 square millimeters, and preferably at least 0.3 square millimeters. Effective apertures 58 are those which have a gray level of 18 or less on a standard gray level scale of 0–255, under the image acquisition parameters described below.

The effective aperture 58 size and percentage open area are determined by the following procedure using the image analysis system described below. The procedure has three principal steps: image acquisition, i.e., obtaining representative images of areas on the surface of the first topsheet 24; image measurement, i.e., measuring the percentage open area of an image and of individual apertures 58 and their perimeters; and data analysis, i.e., exporting the percentage open area, individual aperture 58 area, and perimeter measurements to a spreadsheet where frequency distributions, sum of area distributions, and hydraulic radius computations are made.

An image analysis system having a frame grabber board, microscope, camera and image analysis software is utilized. A model DT2855 frame grabber board available from Data Translation of Marlboro, Mass. is provided. A VH5900 monitor microscope, a video camera, having a VH50 lens with a contact type illumination head available from the Keyence Company of Fair Lawn, N.J. are also provided and used to acquire an image to be saved to computer file. The Keyence microscope acquires the image and the frame grabber board converts the analog signal of this image into computer readable digital format. The image is saved to computer file and measured using suitable software such as the Optimas Image Analysis software, version 3.1, available from the BioScan Company of Edmonds, Wash. In order to use the Optimas Image Analysis software, the computer should have Windows software, version 3.0 or later, available from the Microsoft Corporation of Redmond, Wash. and also have a CPU at least equivalent to the Intel 80386. Any suitable desk top PC may be used, with a 486 DX33 type PC having been found to be particularly suitable. Images being saved to and recalled from file were displayed on a Sony Trinitron monitor model PVM-1343MO with a final display magnification of about 50X.

The image acquisition step, noted above requires 10 different regions from a representative first topsheet 24 sample of a particular type of diaper 20 or from sample material to be tested. Each region is rectangular, measuring about 5.8 millimeters by 4.2 millimeters. The sample is placed on a black mat board to increase the contrast between the apertures 58 and the portion of the sample which defines the apertures 58. The mean gray level and standard deviation of the black mat board were 16 and 4, respectively.

Images are acquired with room lights off using the Keyence monitor microscope mounted on a copystand directly above the sample. The Keyence light source illuminating the sample is adjusted and monitored with the Optimas software to measure the mean gray level and standard deviation of a 0.3 density wedge on a Kodak Gray Scale available from Eastman Kodak Company of Rochester, N.Y. The control of Keyence light source is adjusted so that the mean gray level of the illuminated wedge is 111±1 and the standard deviation is 10±1. All images were acquired during a single time period, and the Keyence light source is monitored by measuring the mean gray level and standard deviation of the wedge throughout the image acquisition process.

In measuring an individual aperture 58, only the effective aperture 58 size is of interest. Measuring the effective aperture 58 size quantifies the aperture 58 size intended to contribute to the porosity of the first topsheet 24, and account for contributions of fibers and fiber bundles which traverse an area intended to be an aperture 58. An effective aperture 58 is any hole through the first topsheet 24 having a gray level less than or equal to 18 using image acquisition parameters as described herein. Thus, an intended aperture 58 may be divided into plural effective apertures 58 by traverse fibers.

The image analysis software is calibrated in millimeters by a ruler image acquired from the sample images. A 3 by 3 pixel averaging filter found in the Optimas 3.1 Image menu is applied to each saved image to reduce noise. The apertures 58 are detected in the gray level range of 0 through 18. An aperture 58 which is not fully contained within the 5.8 by 4.2 viewing area is not considered in the individual area and perimeter measurements. Therefore, area and perimeter averages and distributions are not affected by apertures 58 which are not wholly contained within the field of view.

However, individual apertures 58 which could not be fully viewed in the image are included in the percentage open area calculation. This difference occurs because the percent open area is simply the image of pixel ratios from 0 through 18 to the total number of pixels in the image. Areas having a gray level 19 or greater were not counted in the open area calculation.

The percentage open area for the average of 10 images for each first topsheet 24 is measured using the Optimas Image Analysis software. The percentage open area is defined as the ratio of the number of pixels having a gray level from 0 through 18 to the total number of pixels for the image. The percentage open area is measured for each image representing one particular region from a first topsheet 24 sample. The percentage open area from each of the 10 individual images is then averaged to yield a percentage open area for the entire sample.

The data analysis is conducted by an Excel spreadsheet, also available from the Microsoft Corporation of Redmond, Wash. The Excel spreadsheet organized the percentage open area, aperture 58 area, and aperture 58 perimeter measurements obtained from the Optimas software. Sample averages and standard deviations, size and frequency distributions of individual aperture 58 areas and hydraulic radius computations (area divided by perimeter) for individual apertures 58 are obtained using the spreadsheet.

Distributions of individual aperture 58 area are also computed using the Excel spreadsheet. The apertures 58 are sorted into bins of certain size ranges. The number of aperture 58 areas falling into certain size ranges of interest is determined as well as the sum of the areas within each range. The ranges are set in increments of 0.05 square millimeters. These areas are expressed as a percentage of the total open area of the sample. The frequency and sum of the area distributions are obtained by combining individual aperture 58 measurements from all 10 images for each sample.

As noted above, the diaper 20 according to the present invention maintains a three-dimensional configuration under load. This configuration provides a void volume for low-viscosity fecal material while the diaper 20 is in use. The three-dimensional configuration may be characterized by the cell depth of the fecal material storage element 25 and/or even the core 28. The fecal material storage element 25 and/or the core 28 are considered as having a three-dimensional configuration only if such components contribute to the capacity of the diaper 20 to hold low-viscosity fecal material away from the wearer after it passes through the first topsheet 24.

Figure 4:
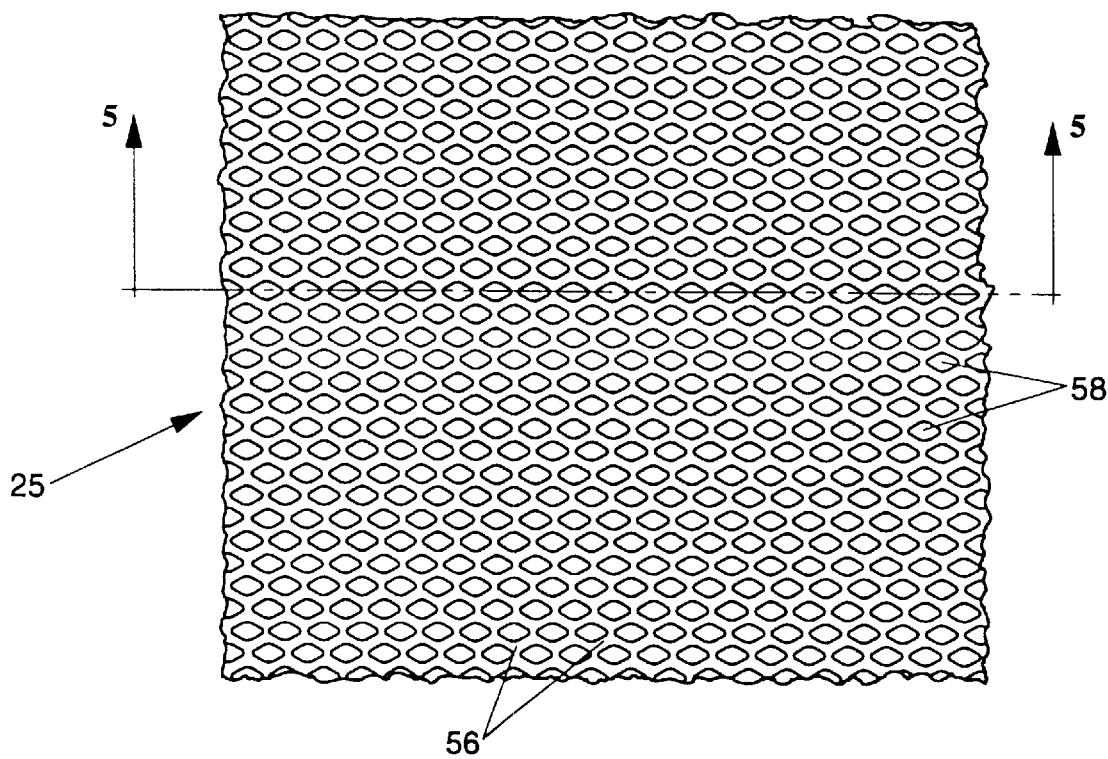
FIG. 4 is a top plan view of an absorbent fecal material storage element for use in a diaper according to the present invention.

The fecal material storage element 25 may either be absorbent or nonabsorbent. If the fecal material storage element 25 is absorbent, it may function as the absorbent core 28. A material suitable for an absorbent fecal material storage element 25 is a cellulosic fibrous structure, such as paper. As illustrated in FIG. 4, the cellulosic fibrous structure may be made by having a continuous high basis weight network 56 with discrete regions 58 of low basis weight, or even discrete apertures 58 having a zero basis weight. In a diaper 20 having such a fecal material storage element 25, the low-viscosity fecal material passes through the first topsheet 24 and resides on the fecal material storage element 25. The low basis weight discrete regions 58 or apertures 58 form cells which immobilize the low-viscosity fecal material.

Once the low-viscosity fecal material is immobilized in this position, it does not return to soil or irritate the skin of the wearer. Furthermore, the low viscosity fecal material can be dewatered into separate components by the capillary action of the more fluid components of the low-viscosity fecal material into the cellulosic fibrous material of the fecal material storage element 25.

Figure 5:
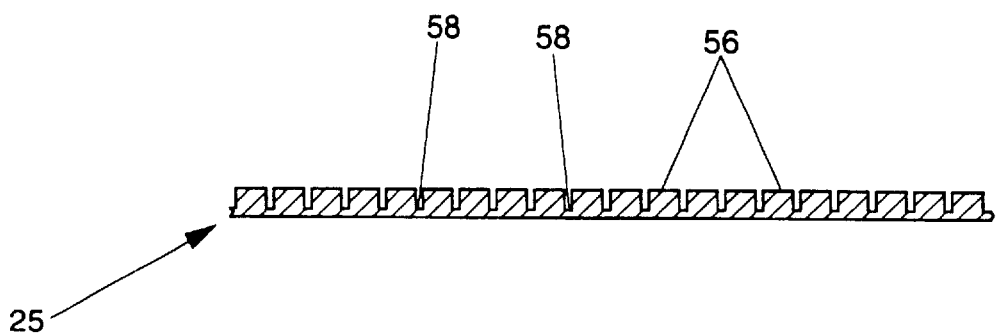
FIG. 5 is a vertical sectional view taken along 5—5 of FIG. 4.

Referring to FIG. 5, the discrete regions 58 in the fecal material storage element 25 may be modeled as blind holes (shown) or through holes. The discrete regions 58 should have an aspect ratio of about 1.0 to about 4.0. The discrete regions 58 should have a major dimension in any direction of at least about 1.5 millimeters (0.08 inches), but no more than about 15 millimeters (0.59 inches). The discrete regions 58 should have a depth, measured while the fecal material storage element 25 is under a load of 31.6 grams per square centimeter (0.45 psi) of at least about 0.75 millimeters (0.03 inches), and preferably at least about 1.5 millimeters (0.06 inches). The ratio of the depth to the major dimension in the X-Y plane should be from about 0.1 to about 2.0.

A suitable absorbent cellulosic fibrous fecal material storage element 25 may have oval shaped low basis weight discrete regions 58 with a major dimension of about 4 to 5 millimeters aligned with the longitudinal axis of the diaper 20, a minor dimension of about 2 to 4 millimeters aligned with the lateral axis of the diaper 20, a depth of about 0.75 millimeters and an overall basis weight, considering both the continuous high basis weight network 56 and the discrete regions 58 of about 98 grams per square meter (60 pounds per 3,000 square feet). A cellulosic fibrous structure suitable for use as the fecal material storage element 25 according to the present invention may be made according to commonly assigned U.S. patent application Ser. No. 07/724,551, Issue Batch No. L87, filed Jun. 28, 1991 in the names of Phan et al. the disclosure of which is incorporated herein by reference. It is noted that this Application matured into U.S. Pat. 5,277,761 issued to Phan et al. on Jan. 11, 1994.

In a second embodiment, a nonabsorbent fecal material storage element 25 may be provided. If a nonabsorbent fecal material storage element 25 is selected, it may be provided in the form of an apertured formed film meeting the caliper requirements described above. Similarly, the apertures 58 of the formed film should meet the size and depth requirements set forth for the discrete regions 58 described above. A suitable formed film is available from Tredegar Corporation of Terre Haute, Ind. under the designation X5790.

Of course, if the fecal material storage element 25 is nonabsorbent, it must be associated with a core 28 which has adequate capacity to absorb and retain the fluids deposited thereon.

The fecal material storage element 25 is preferably only peripherally joined to the first topsheet 24 or, alternatively, may be locally joined to the first topsheet 24 at discrete sites. At most, 50 percent of the fecal material storage element 25 within a minor peripheral region should be joined to the first topsheet 24. The fecal material storage element 25 is joined to the first topsheet 24 in only discrete localized regions inside the peripheral region, to maximize low-viscosity fecal material penetration and to minimize rewet. Rewet occurs when urine or the liquid components of fecal material return to the body facing side (i.e., the first major face) of the first topsheet 24 after the fecal material storage element 25 and core 28 become loaded.

If desired, the first topsheet 24 and the fecal material storage element 25 may be bonded together at sites within the periphery of the diaper 20. If such bonding occurs, preferably the bonding is done at discrete sites. Such bonding should be in a pattern which permits the first topsheet 24 to separate from the fecal material storage element 25 a Z-direction distance of about 0.5 to 7.6 centimeters (0.20 to 3.0 inches). If the bonding sites are too close together, they will create a damming effect, preventing low-viscosity fecal material which is entrapped between the first topsheet 24 and the fecal material storage element 25 from moving in the X-Y direction. In an extreme case, bonding sites which are too close together will prevent or substantially minimize penetration of the low-viscosity fecal material through the first topsheet 24. Alternatively, if the bonding sites are too far apart, excessive Z-direction separation between the first topsheet 24 and the fecal material storage element 25 will occur, allowing the diaper 20 to become unstable and lodge in the gluteal groove of the wearer.

A particularly preferred embodiment utilizes two longitudinally oriented stripes of discrete ultrasonic or adhesive bonds. The discrete bonds have a diameter of about 2 millimeters. Each ultrasonic bond is longitudinally spaced from the adjacent ultrasonic bond on a pitch of about 0.3 centimeters (0.12 inches) and is arranged in a serpentine pattern. For the embodiments described herein, the two longitudinally oriented stripes may be transversely separated by a distance of about 4 centimeters (1.5 inches) on a diaper 20 having a core 28 about 14 centimeters (5.51 inches) in transverse dimension.

Regardless of the bond pattern selected, preferably less than 50 percent and more preferably less than 25 percent of the surface area of the first topsheet 24 is joined to the fecal material storage element 25 between the leg cuffs or between the inner leg cuffs if the diaper 20 has dual leg cuffs.

Preferably a higher percentage of the surface area of the fecal material storage element 25 is joined to the absorbent core 28, if the core 28 is a separate element. If the fecal material storage element 25 is joined to the absorbent core 28, maximum dewatering of the fecal material can occur once the fecal material is immobilized. Preferably the fecal material storage element 25 is joined throughout at least 50 percent of its surface area to the absorbent core 28 by a bond pattern such as a reticulated narrow-bead hot melt adhesive.

The diaper 20 may further comprise elasticized leg cuffs (not shown) which provide improved containment of liquids and other body exudates. Each elasticized leg cuff may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper 20 which provides a contractible leg opening having a side flap and one or more elastic members to provide an elasticized leg cuff (gasketing cuff). Commonly assigned U.S. Pat. 4,909,803 entitled "Disposable Absorbent Article Having Elasticized Flaps" issued to Aziz et al. on Mar. 20, 1990, describes a disposable diaper 20 having "stand-up" elasticized flaps (barrier cuffs) to improve the containment of the leg regions. Commonly assigned U.S. Pat. No. 4,695,278 entitled "Absorbent Article Having Dual Cuffs" issued to Lawson on Sep. 22, 1987, describes a disposable diaper 20 having dual cuffs including a gasketing cuff and a barrier cuff.

The diaper 20 preferably further comprises an elastic waist feature (not shown) that provides improved fit and containment. The elastic waist feature is that portion or zone of the diaper 20 which is intended to elastically expand and contract to dynamically fit the wearer's waist. The elastic waist feature at least extends longitudinally outwardly from at least one of the waist edges of the absorbent core 28 and generally forms at least a portion of the end edge of the diaper 20. Disposable diapers are generally constructed so as to have two elastic waist features, one positioned in the first waist region 27 and one positioned in the second waist region 29, although diapers can be constructed with a single elastic waist feature. Further, while the elastic waist feature or any of its constituent elements can comprise a separate element affixed to the diaper 20, the elastic waist feature is preferably constructed as an extension of other elements of the diaper 20 such as the backsheet 26 or the first topsheet 24, preferably both the backsheet 26 and the first topsheet 24. The elasticized waistband 34 may be constructed in a number of different configurations including those described in U.S. Pat. No. 4,515,595 issued to Kievit et al. on May 7, 1985 and in U.S. patent application Ser. No. 07/715,152; each of these references being incorporated herein by reference. It is noted that a CIP of application Ser. No. 07/715,152 was filed as application Ser. No. 07/750,775 and matured into U.S. Pat. No. 5,151,092 issued to Buell et al. on Sep. 9, 1992.

The diaper 20 also comprises a fastening system 36 which forms a side closure which maintains the first waist region 27 and the second waist region 29 in an overlapping configuration such that lateral tensions are maintained around the circumference of the diaper 20 to maintain the diaper 20 on the wearer. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; commonly assigned U.S. Pat. No. 4,946,527 entitled "Pressure-Sensitive Adhesive Fastener And Method of Making Same" issued to Battrell on Aug. 7, 1990; commonly assigned U.S. Pat. No. 3,848,594 entitled "Tape Fastening System for Disposable Diaper" issued to Buell on Nov. 19, 1974; commonly assigned U.S. Pat. No. B1 4,662,875 entitled "Absorbent Article" issued to Hirotsu et al. on May 5, 1987; and the hereinbefore referenced U.S. patent application 07/715,152; each of which is incorporated herein by reference.

The diaper 20 is preferably applied to a wearer by positioning one of the waist regions, preferably the second waist region 29, under the wearer's back and drawing the remainder of the diaper 20 between the wearer's legs so that the other waist region, preferably the first waist region 27, is positioned across the front of the wearer. The tape tabs 36 of the fastening system are then released from the release portion. The diaperer then wraps the elasticized side panel around the wearer, while still grasping the tab portion. The fastening system is secured to the outer surface of the diaper 20 to effect two side closure.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article for being worn by a wearer, the disposable absorbent article comprising:
   a hydrophobic topsheet;
   a backsheet at least partially peripherally joined to the topsheet; and
   a fecal material storage element intermediate the topsheet and the backsheet, the fecal material storage element having two major faces, a first major face oriented towards the topsheet and a second major face oriented towards the backsheet, whereby the disposable absorbent article has a trans-topsheet capacity greater than about 0.20 grams per square inch.

2. The disposable absorbent article of claim 1 wherein at least a portion of the hydrophilic topsheet is treated to be hydrophilic.

3. The disposable absorbent article of claim 1 wherein the hydrophobic topsheet is selected from the following group: apertured plastic films and woven or nonwoven webs of synthetic fibers or a combination of natural and synthetic fibers.

4. The disposable absorbent article of claim 1 wherein the topsheet is bonded to the fecal material storage element at discrete sites to permit the topsheet to separate from the fecal material storage element between about 0.5 and about 7.6 cm.

5. The disposable absorbent article of claim 1 wherein the fecal material storage element comprises a cellulosic fibrous structure.

6. The disposable absorbent article of claim 1 wherein the topsheet comprises apertures having an effective aperture size of at least 0.3 square mm.

7. The disposable absorbent article of claim 1 wherein the fecal material storage element maintains a 3-dimensional configuration under load.

8. The disposable absorbent article of claim 1 wherein the disposable absorbent article has a trans-topsheet capacity of at least about 0.40 grams per square inch.

9. The disposable absorbent article of claim 1 wherein the disposable absorbent article has a trans-topsheet capacity of at least about 0.60 grams per square inch.

10. The disposable absorbent article of claim 1 wherein at least about 4 square inches of the disposable absorbent article has the trans-topsheet capacity.

11. The disposable absorbent article of claim 1 wherein at least about 20 square inches of the disposable absorbent article has the trans-topsheet capacity.

12. The disposable absorbent article of claim 1 wherein the topsheet and the fecal material storage element are joined at discrete sites spaced at least about 0.5 inches apart.

13. The disposable absorbent article of claim 1 wherein the fecal material storage element comprises blind holes having a depth of at least about 0.75 millimeters while the fecal material storage element is under a load of 31.6 grams per square centimeter.

14. The disposable absorbent article of claim 1 further comprising an absorbent core intermediate the fecal material storage element and the backsheet.

15. A disposable absorbent article for being worn by a wearer, the disposable absorbent article comprising:
   a hydrophobic topsheet;
   an absorbent core intermediate the topsheet and the backsheet;
   a fecal material storage element intermediate the topsheet and the core, the fecal material storage element having two major faces, a first major face oriented towards the topsheet and a second major face oriented towards the core, wherein less than fifty percent of the surface area of the first major surface of the fecal material storage element is bonded to the topsheet and at least fifty percent of the surface area of the second major surface of the fecal material storage element is bonded to the core, the disposable absorbent article having a trans-topsheet capacity greater than about 0.30 grams per square inch; and
   a backsheet at least partially peripherally joined to one of the topsheet and the fecal material storage element.

16. The disposable absorbent article of claim 15 wherein at least 15 square inches of the disposable absorbent article has a trans-topsheet capacity greater than about 0.30 grams per square inch.

17. A disposable absorbent article for being worn by a wearer, the disposable absorbent article comprising:
- a hydrophobic topsheet including apertures having an effective aperture size of at least 0.3 square mm.;
- a backsheet at least partially peripherally joined to the topsheet; and
- a fecal material storage element intermediate the topsheet and the backsheet, the fecal material storage element having two major faces, a first major face oriented towards the topsheet and a second major face oriented towards the backsheet, wherein the disposable absorbent article has a trans-topsheet capacity greater than about 0.20 grams per square inch; and
- wherein the topsheet is bonded to the fecal material storage element at discrete sites to permit the topsheet to separate from the fecal material storage element between about 0.5 and about 7.6 cm.

18. The disposable absorbent article of claim 17 wherein at least a portion of the hydrophobic topsheet is treated to be hydrophilic.

19. The disposable absorbent article of claim 17 wherein the hydrophobic topsheet is selected from the following group: apertured plastic films and woven or nonwoven webs of synthetic fibers or a combination of natural and synthetic fibers.

20. The disposable absorbent article of claim 17 further comprising an absorbent core intermediate the fecal material storage element and the backsheet.

* * * * *

UNITED STATES PATENT AND TRADEMARK OFFICE
CERTIFICATE OF CORRECTION

PATENT NO. : 6,414,215 B1
DATED : July 2, 2002
INVENTOR(S) : Donald C. Roe

It is certified that error appears in the above-identified patent and that said Letters Patent is hereby corrected as shown below:

<u>Column 16,</u>
Line 49, Claim 15 should read

-- 15. A disposable absorbent article for being worn by a wearer, the disposable absorbent article comprising:
    a hydrophobic topsheet;
    a backsheet;
    an absorbent core intermediate the topsheet and the backsheet; and
    a fecal material storage element intermediate the topsheet and the core, the fecal material storage element having two major faces, a first major face oriented towards the topsheet and a second major face oriented towards the core, wherein less than fifty percent of the surface area of the first major surface of the fecal material storage element is bonded to the topsheet and at least fifty percent of the surface area of the second major surface of the fecal material storage element is bonded to the core, the disposable absorbent article having a trans-topsheet capacity greater than about 0.30 grams per square inch;
    wherein the backsheet is at least partially peripherally joined to one of the topsheet and the fecal material storage element. --

Signed and Sealed this

Twenty-seventh Day of May, 2003

JAMES E. ROGAN
*Director of the United States Patent and Trademark Office*